US00PP26205P3

(12) United States Plant Patent

Zaiger et al.

(10) Patent No.: US PP26,205 P3

(45) Date of Patent: Dec. 15, 2015

(54) INTERSPECIFIC TREE NAMED 'WESTON'

(50) Latin Name: **Interspecific *Prunus* species**
Varietal Denomination: WESTON

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 210 days.

(21) Appl. No.: 13/998,844

(22) Filed: Dec. 16, 2013

(65) Prior Publication Data

US 2015/0173266 P1 Jun. 18, 2015

(51) Int. Cl.
*A01H 5/08* (2006.01)

(52) U.S. Cl.
USPC ..... Plt./180

(58) Field of Classification Search
USPC ..... Plt./180
See application file for complete search history.

*Primary Examiner* — Anne Grunberg

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Heavy and regular bearer of large size fruit.
3. Relatively uniform ripening of fruit throughout the tree.
4. Fruit with very good flavor and eating quality.
5. Fruit with good balance between acid and sugar.
6. Fruit with an attractive orange skin and flesh color.

1 Drawing Sheet

Botanical designation: Interspecific *Prunus* species.
Variety denomination: 'WESTON'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecifics and apricots, which are known to us, and mentioned herein, 'Wescot' Interspecific (U.S. Plant Pat. No. 16,597) and our non-patented proprietary interspecific seedlings '318LN552', '19Z215' and the non-patented proprietary apricot seedlings with the field identification numbers '285LP23', '101LE490' and '160LH337'.

STATEMENT REGARDING FEDERALLY SPONSORED RESEARCH AND DEVELOPMENT

Not applicable.

ORIGIN OF THE VARIETY

The new and distinct variety of interspecific tree [(*Prunus armeniaca*×*Prunus salicina*)×*Prunus armeniaca*] was developed by us in our experimental orchard located near Modesto, Calif. as a first generation cross between our proprietary non-patented interspecific selection with the field identification number '318LN552' and the non-patented apricot selection '285LP23'. The seed parent '318LN552' interspecific (non-patented) originated as an open pollinated seedling selection from our non-patented proprietary interspecific seedling '19Z215'. The non-patented apricot pollen parent '285LP23' originated from a first generation cross between our non-patented proprietary apricot selections '101LE490' and '160LH337'. A large number of these first generation seedlings were grown on their own root system and under close and careful observation the present seedling exhibited desirable fruit and tree characteristics and was selected in 2007 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific tree (Plumcot× Apricot) is of large size, vigorous, upright growth and a regular and productive bearer of large, freestone, orange flesh fruit with very good flavor and eating quality. The fruit is further characterized by having an attractive orange skin color, firm flesh with good handling and shipping quality. In comparison to the interspecific seed parent (318LN552) (non-patented) the new variety sets more fruit per tree and is approximately 12 days later in maturity. In comparison to its non-patented apricot pollen parent (285LP23) the fruit of the new variety is larger in size and has a more attractive orange skin color. In comparison to the commercial variety 'Wescot' Interspecific (U.S. Plant Pat. No. 16,597) the fruit of the new variety is larger in size and is approximately 20 days later in maturity.

DESCRIPTION OF THE PHOTOGRAPH

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color published in 1958.

Tree:

*Size.*—Large, usually pruned to 3 to 3.5 meters in height and width for economical harvesting of fruit. Size varies with different cultural practices.

*Vigor.*—Vigorous, growth of 1.5 to 2 meters the first growing season. Varies slightly with type of soil, fertility and climatic conditions.

*Form.*—Upright, usually pruned to vase shape.

*Branching habit.*—Upright, crotch angle approximately 35°, increases with heavy crop load.

*Productivity.*—Productive, normal fruit thinning necessary for desired market size fruit. Fruit set varies with climatic conditions during bloom season.

*Bearer.*—Regular, adequate fruit set 4 consecutive years. No alternate bearing observed.

*Fertility.*—Self-fertile, sets fruit under bag.

*Density.*—Medium dense, usually pruned to vase shape to increase amount of sunlight to center of tree to enhance fruit color, Brix and health of fruit wood.

*Hardiness.*—Hardy in all stone fruit growing areas of California. Tree grown in USDA Hardiness Zone 9. Winter chilling requirement approximately 900 hours at or below 45° F.

Trunk:

*Size.*—Large. Circumference of 58.4 cm at 23.0 cm above ground on a 6 year old tree.

*Stocky.*—Medium stocky.

*Texture.*—Medium shaggy, roughness increases with age.

*Color.*—Varies from 2.5Y 5/2 to 5Y 4/2.

Branches:

*Size.*—Medium. Average circumference 8.9 cm at 1.2 meters above ground. Crotch angle approximately 35°, increases with heavy crop load.

*Surface texture.*—New growth relatively smooth. Mature growth medium rough, roughness increases with age.

*Lenticels.*—Average number 30 in a 25.8 square cm area. Average length 4.8 mm. Average width 1.9 mm. Color varies from 2.5Y 7/8 to 2.5Y 6/8.

*Color.*—New growth varies from 5GY 5/6 to 7.5R 3/4. Mature growth varies from 7.5YR 2/2 to 10YR 2/2, varies with age of growth.

Leaves:

*Size.*—Large. Average length 98.2 mm. Average width 79.6 mm.

*Form.*—Globose.

*Apex.*—Cuspidate.

*Base.*—Obtuse.

*Margin.*—Doubly serrate.

*Thickness.*—Medium.

*Surface texture.*—Upper surface relatively smooth, slight indentations over midrib and leaf veins, glabrous. Lower surface relatively smooth, except for small ridges created by midrib and pinnate venation, glabrous.

*Petiole.*—Average length 40.9 mm. Average width 1.4 mm. Longitudinally grooved. Surface glabrous. Color varies from 5GY 5/6 to 7.5R 2/6.

*Glands.*—Type — reniform. Size — small to medium. Average length 0.7 mm. Average diameter 0.5 mm. Average number 3, varies from 2 to 4. Located primarily on base of leaf blade and upper portion of petiole. Color 7.5R 2/4.

*Stipules.*—Average number 2. Average length 5.7 mm. Edges — pectinate. Color varies from 5GY 7/6 to 5GY 6/8.

*Color.*—Upper surface varies from 5GY 3/6 to 7.5GY 3/6. Lower surface varies from 5GY 4/4 to 7.5GY 4/4. Midvein color varies from 2.5GY 7/6 to 5GY 5/6.

Flower buds:

*Size.*—Large. Average length 14.3 mm. Average diameter 8.6 mm.

*Hardiness.*—Hardy with respect to California winters.

*Form.*—Conical, becoming elongated just before opening.

*Pedicel.*—Average length 2.1 mm. Average width 1.4 mm. Color varies from 2.5GY 8/6 to 2.5GY 7/6. Surface — glabrous.

*Color.*—Varies from 7.5RP 9/2 to 7.5RP 6/2.

*Number of buds per spur.*—Varies from 7 to 10, average number 8. Varies with age of spur.

Flowers:

*Blooming period.*—Date of First Bloom Feb. 22, 2013. Date of Petal Fall Mar. 4, 2013, varies slightly with climatic conditions.

*Size.*—Medium to large. Average height 17.8 mm. Average diameter 24.7 mm.

*Petals.*—Normally 5, alternately arranged to sepals. Size — medium to large. Average length 12.6 mm. Average width 15.5 mm. Form orbicular. Arrangement — overlapping. Margin — sinuate. Color varies from 7.5RP 9/2 to N 9.5/(white), fades with age of flower.

*Sepals.*—Normally 5, alternately arranged to petals. Size — large. Average length 7.1 mm. Average width 6.8 mm. Shape — ovate. Margin — entire. Both upper and lower surfaces glabrous. Color — upper surface 2.5R 3/8. Lower surface varies from 2.5R 3/8 to 5R 2/6.

*Stamens.*—Average number per flower 31. Average length 12.2 mm. Filament color N 9.5/(white). Anther color varies from 5Y 8/8 to 5Y 8/10.

*Pollen.*—Self-fertile. Color varies from 5Y 8/8 to 5Y 8/10.

*Pistil.*—Number — normally one. Surface — pubescent. Average length 11.6 mm. Position of stigma an average of 4.4 mm below anthers. Color varies from 7.5Y 8.5/4 to 7.5Y 8/4.

*Fragrance.*—Heavy.

*Color.*—Varies from 7.5RP 9/2 to N 9.5/(white).

*Pedicel.*—Average length 2.6 mm. Average width 1.4 mm. Color varies from 10Y 7/6 to 2.5GY 7/6.

*Number flowers per flower bud.*—Usually 1, varies from 1 to 2.

Fruit:

*Maturity when described.*—Firm ripe.

*Date of first picking.*—Jun. 10, 2013.

*Date of last picking.*—Jun. 18, 2013, varies slightly with climatic conditions.

*Size.*—Large. Average diameter axially 72.9 mm. Average transversely in suture plane 71.0 mm. Average across suture plane 65.3 mm. Average weight 190.3 grams, varies slightly with fertility of the soil, amount of thinning and climatic conditions.

*Form.*—Elongated.

*Suture.*—Lipped, extends from base to apex.

*Ventral surface.*—Lipped, well sealed.

*Apex.*—Slightly retuse.

*Base.*—Retuse.

*Stem cavity.*—Rounded to slightly elongated in suture plane. Average depth 7.2 mm. Average diameter 7.0 mm.

Stem:

*Size.*—Small. Average length 8.1 mm. Average diameter 3.9 mm.

*Color.*—Varies from 5GY 5/6 to 5GY 5/8.

Flesh:

*Ripens.*—Evenly.

*Texture.*—Firm, meaty.

*Fibers.*—Few, small, tender.

*Firmness.*—Firm, comparable to other commercial apricots.

*Aroma.*—Moderate.

*Amydgalin.*—Undetected.

*Eating quality.*—Very good.

*Flavor.*—Very good, good balance between acid and sugar.

*Juice.*—Moderate amount, enhances flavor.

*Brix.*—Average Brix 16.0°, varies slightly with amount of fruit per tree and climatic conditions.

*Color.*—Varies from 3.75YR 5/12 to 6.25YR 6/12.

*Pit cavity.*—Average length 35.0 mm. Average width 32.0 mm. Average depth 9.0 mm. Color varies from 6.25YR 6/12 to 3.75YR 5/12.

Skin:

*Thickness.*—Medium.

*Surface.*—Slightly waffled.

*Pubescence.*—Moderate amount, short in length.

*Tendency to crack.*—None.

*Color.*—Ground color varies from 2.5YR 5/10 to 6.25YR 6/12. Overspread with 5R 3/8 where exposed to the sun.

*Tenacity.*—Tenacious to flesh.

*Astringency.*—Slight to none.

Stone:

*Type.*—Freestone.

*Size.*—Large. Average length 32.6 mm. Average width 27.2 mm. Average thickness 13.8 mm.

*Form.*—Ovoid.

*Base.*—Usually flat, varies on some stones from flat to slightly rounded.

*Apex.*—Rounded.

*Surface.*—Slightly pitted throughout, pits vary from round to elongated.

*Sides.*—Unequal, one side extending further from suture plane.

*Ridges.*—Extend from base to apex.

*Tendency to split.*—None.

*Color.*—Varies from 10YR 4/2 to 10YR 4/4 when dry.

Kernel:

*Size.*—Large. Average length 21.1 mm. Average width 15.1 mm. Average depth 7.5 mm.

*Form.*—Ovoid.

*Viability.*—Viable, complete embryo development.

*Skin color.*—Varies from 7.5YR 9/2 to 10Y 9/2.

Use: Dessert.

*Market.*—local and long distance.

Keeping quality: Good, held firm in cold storage 3 weeks at 38° to 42° F. without internal breakdown of flesh or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

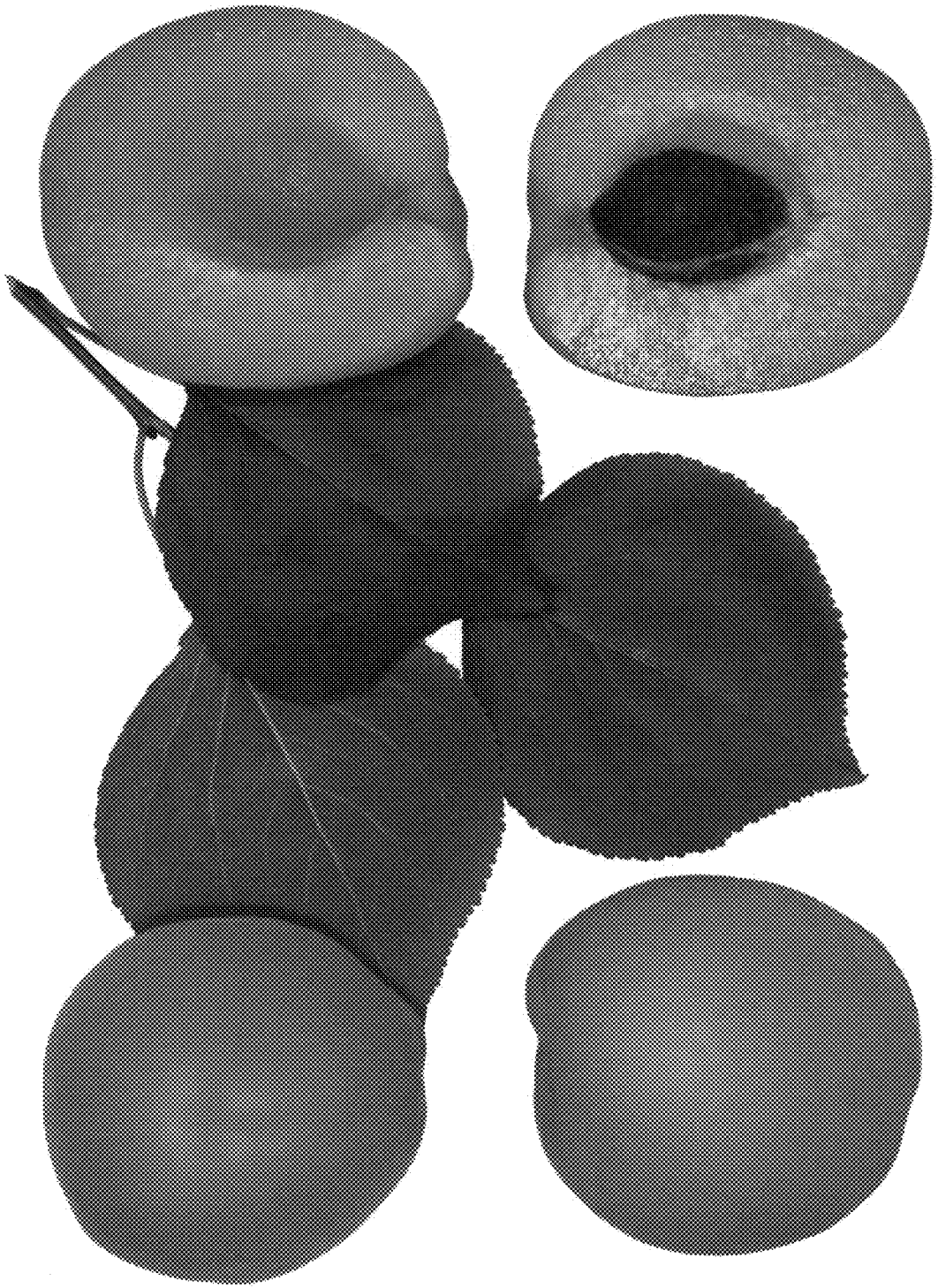

* * * * *